(12) United States Patent
Richard

(10) Patent No.: US 7,018,427 B2
(45) Date of Patent: Mar. 28, 2006

(54) DYEING COMPOSITION CONTAINING A PARA-AMINOPHENOL OR PARA-PHENYLENEDIAMINE COMPOUND SUBSTITUTED WITH A SILANE RADICAL

(75) Inventor: Hervé Richard, Villepinte (FR)

(73) Assignee: L'Oreal S.A., Paris (FR)

( * ) Notice: Subject to any disclaimer, the term of this patent is extended or adjusted under 35 U.S.C. 154(b) by 225 days.

(21) Appl. No.: 10/259,298

(22) Filed: Sep. 30, 2002

(65) Prior Publication Data

US 2003/0150066 A1 Aug. 14, 2003

(30) Foreign Application Priority Data

Sep. 28, 2001 (FR) ................... 01 12523

(51) Int. Cl.
*A61K 7/13* (2006.01)
(52) U.S. Cl. .................. 8/405; 406/410; 406/411; 406/421; 406/423; 406/581; 556/400
(58) Field of Classification Search .................. 8/405, 8/406, 410, 411, 421, 423, 581; 556/400
See application file for complete search history.

(56) References Cited

U.S. PATENT DOCUMENTS

| | | | |
|---|---|---|---|
| 3,627,800 A | 12/1971 | Owen et al. ............ | 260/448.2 |
| 3,898,255 A | 8/1975 | Meiller ................... | 260/448.2 |
| 4,003,699 A | 1/1977 | Rose et al. .................... | 8/10.2 |
| 4,823,985 A | 4/1989 | Grollier et al. ................. | 222/1 |
| 5,061,289 A | 10/1991 | Clausen et al. ................. | 8/405 |
| 5,380,340 A | 1/1995 | Neunhoeffer et al. .......... | 8/409 |
| 5,676,706 A | 10/1997 | Akram et al. ................... | 8/416 |
| 5,766,576 A | 6/1998 | Löwe et al. ................... | 424/62 |
| 6,027,537 A | 2/2000 | Leduc et al. .................... | 8/405 |
| 6,099,592 A | 8/2000 | Vidal et al. ..................... | 8/409 |
| 6,099,593 A | 8/2000 | Terranova et al. .............. | 8/409 |
| 6,203,578 B1 | 3/2001 | Leduc et al. .................... | 8/405 |
| 2002/0155082 A1 | 10/2002 | Richard et al. .......... | 424/70.12 |

FOREIGN PATENT DOCUMENTS

| | | |
|---|---|---|
| DE | 20 16 369 | 2/1971 |
| DE | 23 59 399 | 6/1975 |
| DE | 38 43 892 | 6/1990 |
| DE | 41 33 957 | 4/1993 |
| DE | 195 43 988 | 5/1997 |
| DE | 201 11 038 | 10/2001 |
| EP | 0 014 599 | 8/1980 |
| EP | 0 313 152 | 4/1989 |
| EP | 0 404 134 | 12/1990 |
| EP | 0 650 970 | 5/1995 |
| EP | 0 770 375 | 5/1997 |
| FR | 2 275 252 | 1/1976 |
| FR | 2 586 913 | 3/1987 |
| FR | 2 733 749 | 11/1996 |
| FR | 2 750 048 | 12/1997 |
| GB | 2018798 | 3/1979 |
| JP | S54-148820 | 11/1979 |
| JP | 61-112086 | 5/1986 |
| JP | 2-19576 | 1/1990 |
| JP | 5-163124 | 6/1993 |
| JP | H08-208568 | 8/1996 |
| JP | H11-506135 | 9/1997 |
| JP | S50-30851 | 2/1998 |
| JP | H10-147589 | 6/1998 |
| WO | WO 94/08969 | 4/1994 |
| WO | WO 94/08970 | 4/1994 |
| WO | WO 96/15765 | 5/1996 |
| WO | WO 97/34904 * | 9/1997 |
| WO | WO 01/66069 | 9/2001 |

OTHER PUBLICATIONS

Tadashi Hashimoto and Michiko Seki: Synthesis of Organosilicon Compounds. VIII 1961, 81, 204-9 (Citation 1).*
Tadashi Hashimoto and Michiko Seki: Synthesis of Organosilicon Compounds. VII 1960, 81, 1399-1404 (Citation 2).*
Giuseppe Bartoli et al., "Intramolecular Peterson Olefination of ortho-Trimethylsilylmethyl Anilides: a New Synthesis of N-Methylindoles," Journal of the Chemical Society, No. 12, Jun. 15, 1988, pp. 807-808.
English language Derwent Abstract of FR 2 275 252, Jan. 16, 1976.
English language Derwent Abstract of JP 61-112086, May 30, 1986.
English language Derwent Abstract of DE 201 11 038, Oct. 4, 2001.
English language Derwent Abstract of EP 0 770 375, May 2, 1997.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

A dyeing composition comprising at least one oxidation base chosen from para-aminophenol and para-phenylenediamine compounds substituted with a silane radical, and the dyeing method using this composition are disclosed. This composition is, for example, useful for dyeing keratinous fibers. The para-aminophenol and para-phenylenediamine compounds substituted with a silane radical are also disclosed.

22 Claims, No Drawings

OTHER PUBLICATIONS

English language Derwent Abstract of JP 2-19576, Jan. 23, 1990.
English language Derwent Abstract of JP 5-163124, Jun. 29, 1993.
First Office Action issued on Japanese Patent Application No. 2002-284272, Ref. No.: F10705A1, Oct. 26, 2004.
Chemical Abstracts 55:75877; Copyright 2004 ACS on STN International; Syntheses of organosilicon compounds; Hashimoto, T., et al.
Chemical Abstracts 55:27658; Copyright 2004 ACS on STN International; Synthesis of organosilicon compounds; Hashimoto, T., et al.

* cited by examiner

DYEING COMPOSITION CONTAINING A PARA-AMINOPHENOL OR PARA-PHENYLENEDIAMINE COMPOUND SUBSTITUTED WITH A SILANE RADICAL

The present invention relates to a dyeing composition comprising at least one oxidation base chosen from para-phenylenediamine and para-aminophenol compounds substituted with a silane radical, and the dyeing method using this composition.

It is known in the art to dye keratinous fibres, for example, human hair, with dyeing compositions containing oxidation dye precursors, generally called oxidation bases, for example, ortho- and para-phenylenediamines, ortho- and para-aminophenols, and heterocyclic compounds. Such oxidation bases are colourless or weakly coloured compounds that combined with oxidizing agents can give rise, through a process of oxidative composition, to coloured compounds.

Various shades may be obtained with these oxidation bases when they are combined with couplers or colour modifiers. The couplers or colour modifiers can be chosen, for example, from aromatic meta-diamines, meta-aminophenols, meta-diphenols, and certain heterocyclic compounds, for example, indolic compounds.

The variety of molecules used in oxidation bases and couplers can allow a rich palette of colours to be obtained.

The so called "permanent" colour obtained using such oxidation dyes should satisfy a number of requirements. It should be without toxicological drawbacks, should enable shades to be obtained in the desired intensity, and should exhibit good resistance towards external agents such as light, adverse weather conditions, washing, permanent waving, perspiration, and rubbing.

Moreover, the dyes should make it possible to cover white hair, and should be as least selective as possible, minimizing the difference in colour along the same keratinous fibre, which may indeed be differently sensitized (i.e. damaged) between its tip and its root.

One purpose of the present invention is to provide novel compositions for the oxidation dyeing of keratinous fibres using oxidation bases, which, for example, can be reactive, can have powerful dyes, can be not very selective, can be resistant to external agents such as shampoos and light, and can generate intense colours in varied shades.

Therefore, one aspect of the invention is a dyeing composition comprising, at least one oxidation base chosen from compounds corresponding to the following formula (I) and the corresponding cosmetically acceptable salts:

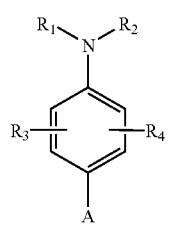

(I)

wherein:
A is chosen from OH and $NH_2$;
$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;

$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;

Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;

Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals and Y is as defined above;

B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B, wherein B, Y, Z are as defined above.

In the above definitions, the alkyl radicals and groups are chosen from linear and branched radicals and groups, and comprise, unless otherwise stated, from 1 to 8 carbon atoms, for example, from 1 to 6 carbon atoms, such as methyl, ethyl, n-propyl, isopropyl, and butyl.

An alkoxy radical is an —O-Alkyl radical, wherein the term "alkyl" is as defined above.

According to one embodiment of the present invention, $R_1$ is a hydrogen atom and $R_2$, $R_3$, and $R_4$ are as defined above, for example, at least one of the groups $R_3$ and $R_4$ is a hydrogen atom.

According to another embodiment of the present invention, $R_1$ and $R_2$ are each a hydrogen atom and the —Z—B radical is on the benzene ring.

According to another embodiment of the present invention, $R_1$ and $R_2$ may form, together with the nitrogen atom to which they are attached, a 5- or 6-membered heterocycle, wherein the heterocycle is substituted with a group —Z—B, $R_3$ and $R_4$ are as defined above. According to this embodiment, $R_3$ and $R_4$ are, for example, each a hydrogen atom.

Among the compounds of formula (I), mention may be made, for example of:

2-trimethylsilanylmethoxy-para-phenylenediamine:

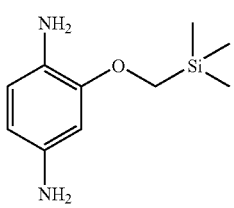

-continued

N-trimethylsilanylmethyl-para-phenylenediamine:
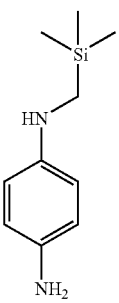

2-[(trimethylsilanyl)ethyl]-para-phenylenediamine:
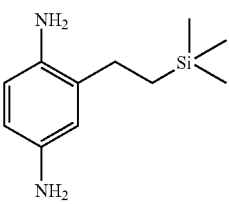

N-trimethylsilanylpropyl-para-phenylenediamine:
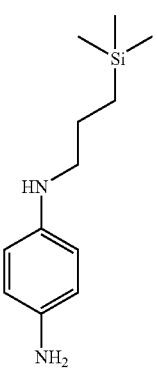

2-(trimethylsilanyl)-para-phenylenediamine:
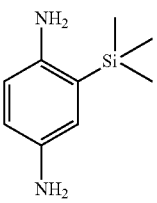

2,5-di-(trimethylsilanyl)-para-phenylenediamine:
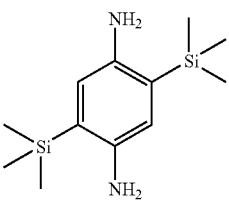

2-trimethylsilanylethoxy-para-phenylenediamine:
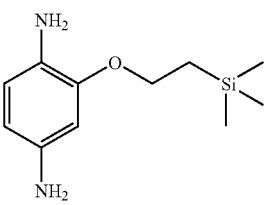

-continued 4-amino-3-(trimethylsilanylmethyl)-phenol
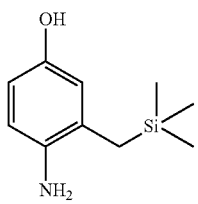

4-amino-3-(trimethylsilanyl)phenol:
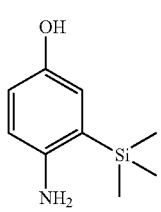

According to the present invention, the at least one oxidation base is generally present in the dyeing composition of the invention in an amount, for example, ranging from 0.0005 to 12% by weight relative to the total weight of the dyeing composition, for example, from about 0.005 to about 6% by weight relative to the total weight of the dyeing composition.

The compounds of formula (I) according to the present invention may be obtained from the general methods of preparation known to persons skilled in the art, for example, by reduction of the corresponding silane-containing para-nitroaniline or silane-containing para-nitrophenol compounds.

This reduction step makes it possible to obtain a primary aromatic amine which confers on the synthesized compound its oxidation base character. This step is optionally followed by salification.

For convenience, this step is normally the final step of the synthesis. However, this reduction may occur earlier in the succession of reactions leading to the preparation of the compounds of formula (I). In that case, according to well-known methods, it is necessary to protect the primary amine created, for example, by a step, such as an acetylation step or a benzenesulfonation step, and then to carry out the desired substitution(s) or modification(s), for example, an alkylation, a Grignard reaction, nucleophilic substitution reactions with the silane derivative(s), or other reactions well known to a person skilled in the art, and to finish by deprotecting the amine functional group, in general, in an acidic medium.

The dyeing composition of the present invention is a cosmetic composition which can be useful for dyeing keratinous fibres, for example, human keratinous fibres such as hair. It may also be useful in the make-up field.

In addition to the compounds described above, the composition of the present invention may further comprise at least one additional oxidation base chosen from the oxidation bases conventionally used in oxidation dyeing, for example, para-phenylenediamines, bisphenylalkylenediamines, para-aminophenols, ortho-aminophenols, heterocyclic bases, and the cosmetically acceptable salts of these compounds.

Among the para-phenylenediamines, mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5- dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and their acid addition salts.

Among the para-phenylenediamines, mention may also be made, for example, of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their acid addition salts.

Among the bis-phenylalkylenediamines, mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their acid addition salts.

Among the para-aminophenols, mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their acid addition salts.

Among the ortho-aminophenols, mention may be made, for example, of 2-aminophenol, 2-amino-5-methylphenol, 2-amino-6-methylphenol, 5-acetamido-2-aminophenol, and their acid addition salts.

Among the heterocyclic bases, mention may be made, for example, of pyridine derivatives, pyrimidine derivatives, and pyrazole derivatives.

Among the pyridine derivatives, mention may be made, for example, of the compounds described in Patents GB 1,026,978 and GB 1,153,196, for example, 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts.

Among the pyrimidine derivatives, mention may be made, for example, of the compounds described in Patents DE 2,359,399, JP 88-169,571, JP 05-163,124, and EP 0,770,375, and Patent Application WO 96/15765, for example, 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives, for example, those found in Patent Application FR-A-2,750,048 and among which mention may be made, for example, of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxy-ethyl)amino]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, their tautomeric forms, when a tautomeric equilibrium exists, and their acid addition salts.

Among the pyrazole derivatives, mention may be made, for example, of the compounds described in Patents DE 3,843,892, DE 4,133,957 and Patent Applications WO 94/08969, WO 94/08970, FR-A-2,733,749 and DE 195 43 988, for example, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their acid addition salts.

The composition according to the invention may further comprise at least one coupler conventionally used for dyeing keratinous fibres. Among the conventionally used couplers, mention may be made, for example, of meta-phenylenediamines, meta-aminophenols, meta-diphenols, naphthalene couplers, heterocyclic couplers, and the cosmetically acceptable salts of these compounds.

Mention may further be made, for example, of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis-(β-hydroxyethyl-amino)toluene, and their addition salts.

In the composition of the present invention, the at least one coupler is present, for example, in an amount ranging from about 0.001 to about 10% by weight relative to the total weight of the dyeing composition, and further, for example, from 0.005 to 6% by weight relative to the total weight of the dyeing composition. The at least one additional oxidation base is present in an amount ranging, for example, from about 0.001 to about 10% by weight relative to the total weight of the dyeing composition, and further, for example, from 0.005 to 6% by weight of the total weight of the dyeing composition.

The salts that can be cosmetically used in the context of the composition according to the invention for oxidation bases and couplers may, for example, be chosen from the acid addition salts, for example, hydrochlorides, hydrobromides, sulfates, citrates, succinates, tartrates, lactates, tosylates, benzenesulfonates, phosphates, and acetates, and the base addition salts, for example, sodium hydroxide, potassium hydroxide, aqueous ammonia, amines, and alkanolamines.

The composition in accordance with the invention may further comprise at least one direct dye that may, for example, be chosen from nitro dyes of the benzene series, cationic direct dyes, azo direct dyes, and methine direct dyes.

The appropriate medium for dyeing, also called dye carrier, generally consists of water or of a mixture of water and at least one organic solvent to solubilize the compounds which might not be sufficiently soluble in water. For the organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, and aromatic alcohols such as benzyl alcohol and phenoxyethanol, and mixtures thereof.

The at least one organic solvent may be present in an amount, for example, ranging from about 1 to about 40% by weight relative to the total weight of the dyeing composition, and further, for example, from about 5 to about 30% by weight relative to the total weight of the dyeing composition.

The dyeing composition in accordance with the invention may also comprise at least one adjuvant chosen from various adjuvants conventionally used in compositions for dyeing hair, such as anionic, cationic, non-ionic, amphoteric and zwitterionic agents, and mixtures thereof, anionic, cationic, non-ionic, amphoteric and zwitterionic polymers, and mixtures thereof, inorganic and organic thickening agents, and, for example anionic, cationic, non-ionic and amphoteric associative polymeric thickeners, antioxidants, penetrating agents, sequestrants, perfumes, buffers, dispersing agents, conditioning agents, for example, volatile and non-volatile, modified and unmodified silicones, film-forming agents, ceramides, preservatives, and opacifying agents.

The at least one adjuvant may be present in an amount ranging from 0.01 to 20% by weight relative to the weight of the composition.

Of course, persons skilled in the art will be careful to choose these optional additional compounds such that the advantageous properties intrinsically attached to the oxidation dyeing composition in accordance with the invention are not, or are not substantially, impaired by the addition envisaged.

The pH of the dyeing composition in accordance with the invention ranges, for example, from about 3 to about 12, and further, for example, from about 5 to about 11. The pH may be adjusted to the desired value by means of acidifying or alkalinizing agents customarily used in dyeing keratinous fibres, or by using conventional buffer systems.

Among the acidifying agents, mention may be made, for example, of inorganic or organic acids such as hydrochloric acids, orthophosphoric acids, sulphuric acids, carboxylic acids, such as acetic acids, tartaric acids, citric acids, lactic acids, and sulphonic acids.

Among the alkalinizing agents, mention may be made, for example, of aqueous ammonia, alkali metal carbonates, alkanolamines such as mono-, di- and triethanolamines and derivatives thereof, sodium or potassium hydroxides and compounds of the following formula (III):

wherein W is a propylene residue that is optionally substituted with a group chosen from hydroxyl and $C_1$–$C_4$ alkyl radicals; $R_a$, $R_b$, $R_c$ and $R_d$, which may be identical or different, are chosen from hydrogen, $C_1$–$C_4$ alkyl, and $C_1$–$C_4$ hydroxyalkyl radicals.

The dyeing composition according to the invention may exist in various forms such as liquids, creams, gels, or any other form appropriate for dyeing keratinous fibres such as human hair.

Another aspect of the invention is a method for dyeing keratinous fibres, and, for example, human keratinous fibres such as hair, using the dyeing composition as defined above.

According to this method, the composition as defined above is applied to the fibres, and the colour is developed using an oxidizing agent. The colour may be developed at acidic, neutral, or alkaline pH, and the oxidizing agent may be added to the composition at the time of use, or the oxidizing agent may be used as an ingredient of an oxidizing composition applied simultaneously or sequentially to the composition of the invention.

For example, in one embodiment of the present invention, the composition is mixed, for example, at the time of use, with a composition comprising, in an appropriate medium for dyeing, at least one oxidizing agent, wherein this oxidizing agent is present in a sufficient amount to develop a colour. The mixture obtained is then applied to the keratinous fibres. After an exposure time approximately ranging from 3 to 50 minutes, and, for example, approximately ranging from 5 to 30 minutes, the keratinous fibres are rinsed, washed with shampoo, rinsed again, and then dried.

The oxidizing agents conventionally used for the oxidation dyeing of keratinous fibres may be, for example, hydrogen peroxide, urea peroxide, alkali metal bromates, persalts, such as perborates and persulphates, peracids and oxidase enzymes among which mention may be made, for example, of peroxidases, oxidoreductases containing two electrons such as uricases, and oxygenases containing four electrons such as laccases.

The oxidizing composition may also comprise at least one adjuvant chosen from various adjuvants conventionally used in hair-dyeing compositions and as defined above.

The pH of the oxidizing composition comprising at least one oxidizing agent is such that after mixing with the dyeing composition, the pH of the resulting composition applied to the keratinous fibres may, for example, range from about 3 to about 12, and further, for example, range from 5 to 11. The pH may be adjusted to the desired value by means of acidifying or alkalinizing agents customarily used in dyeing keratinous fibres and as defined above.

The composition which is finally applied to the keratinous fibres may be provided in various forms, for example, liquids, creams, gels, and in any other form appropriate for dyeing keratinous fibres and, for example, human hair.

Another aspect of the invention is a multi-compartment device or dyeing kit comprising a first compartment comprising the dyeing composition defined above and a second compartment comprising an oxidizing composition. This device may be equipped with a means by which it is possible to deliver the desired mixture onto the hair, such as the devices described in Patent FR-2,586,913.

Finally, another aspect of the invention is the coloured product resulting from the oxidation of the composition according to the present invention. These coloured products may, for example, be provided in the form of pigments and may be used as a direct dye for the direct dyeing of hair and alternatively may be incorporated into cosmetic products such as make-up products.

The following examples serve to illustrate, but not to limit, the invention.

EXAMPLES

Examples of Syntheses

Example 1

Synthesis of 2-trimethylsilanylmethoxy-para-phenylenediamine dihydrochloride

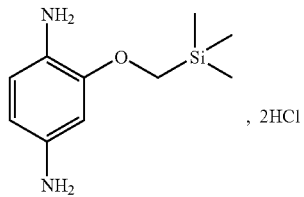

a/First step: Synthesis of N-(4-nitro-2-trimethylsilanyl-methoxyphenyl)acetamide A mixture of 84.9 g (0.433 mol) of N-(2-hydroxy-4-nitrophenyl)acetamide and 144 g (0.44 mol) of caesium carbonate in 350 ml of anhydrous DMF, under a nitrogen atmosphere, was heated to 65° C. with stirring. 58.4 g (0.476 mol) of chloromethyltrimethylsilyl were added to this heterogeneous mixture over 4 hours, with stirring, dropwise at 65° C. The reaction mixture was cooled and poured into 700 ml of ice-cold water, with stirring. The precipitate formed was filtered, washed with water, and dried. 119 g (yield of 97%) of N-(4-nitro-2-trimethylsilanylmethoxyphenyl)acetamide were obtained in the form of a light brown powder.

Melting point: 128° C.

This product was used as is in the next step.

b/Second step: Synthesis of 4-nitro-2-trimethylsilanyl-methoxyphenylamine 104 g (0.368 mol) of the preceding product were solubilized, in the hot state (65° C.), with stirring and under a nitrogen atmosphere, in 600 ml of methanol. A solution of sodium methoxide in methanol (3.2 g of sodium methoxide at 30% are diluted in 80 ml of methanol, that is 17 meq of sodium methoxide) was added dropwise to the reaction mixture over 2 hours 30 minutes. The mixture was cooled and was poured into 2 liters of water, with stirring. The yellow solid formed was filtered, washed with water, and dried under vacuum. 95.5 g (yield of 99%) of 4-nitro-2-trimethylsilanylmethoxyphenylamine were obtained in the form of yellow flakes.

Melting point: 87° C.

This product was used as is in the next step.

c/Third step: Synthesis of 2-trimethylsilanylmethoxy-para-phenylenediamine dihydrochloride 35.7 g (0.138 mol) of the preceding derivative, 3.5 g of 5% palladium on carbon moistened with 50% of water and 350 ml of absolute ethanol were introduced into a 500 ml hydrogenator. The hydrogenator was closed and, under hydrogen pressure (5 bar), the mixture was kept at 40° C. for 1 hour. After degassing with nitrogen, the reaction mixture was poured into 200 ml of ethanol containing 26 ml of concentrated hydrochloric acid (that is 280 meq). The solvent was evaporated to dryness and dried under vacuum. 38.8 g (yield of 99%) of product were thus obtained in the form of an off-white powder.

Elemental Analysis for $C_{10}H_{16}N_2OSi.2HCl$ Calc:C 42.40; H 7.12; N 9.89; Si 9.91; Cl 25.03 Found:C 42.52; H 7.07; N 9.71; Si 9.50; Cl 25.25

Example 2

Synthesis of N-trimethylsilanylmethyl-para-phenylenediamine dihydrochloride

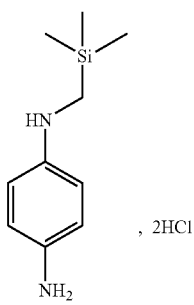

a/First step: Synthesis of N-(4-nitrophenyl)-N-trimethylsilanylmethylamine 5 g (0.048 mol) of aminomethyltrimethylsilane were added dropwise over 15 minutes at room temperature to a mixture of 6.83 g (0.048 mol) of 1-fluoro-4-nitrobenzene and 6.68 ml (0.048 mol) of triethylamine dissolved in 25 ml of dichloromethane. The mixture was kept stirred for 6 hours. 50 ml of water were added, and the 2 phases were separated. The aqueous phase was extracted with dichloromethane. The organic phases were combined, washed with water, dried over sodium sulfate, filtered, and then concentrated. The orange-coloured oil obtained was purified on silica (eluant: Heptane/AcOEt 95/5) to give clean fractions which crystallize off N-(4-nitrophenyl)-N-trimethylsilanylmethylamine: weight: 4.15 g (yield of 38%):

Yellow powder. Melting point: 120° C. Mass spectrum: $M^+ + H = 225$.

a/ Second step: Synthesis of N-trimethylsilanylmethyl-para-phenylenediamine dihydrochloride 2.29 g (35 mmol) of zinc powder, 117 mg (2.18 mmol) of ammonium chloride, 7 ml of ethanol at 96° C. and 1 ml of distilled water were introduced into a reactor under bubbling of argon. This mixture was heated at the reflux temperature of ethanol. 1 g (4.45 mmol) of the product of the preceding step was added portionwise over 30 minutes. The mixture was kept under good reflux for 30 minutes. The reaction mixture was filtered in the hot state and 0.3 ml of concentrated hydrochloric acid was rapidly added to the filtrate. The latter, which was violet and then pale yellow in colour, was evaporated to dryness, triturated in cyclohexane and dried under vacuum in the presence of potassium hydroxide pellets at 25° C. 0.87 g (yield of 58%) of product was thus obtained in the form of a pale yellow powder.

Elemental Analysis for $C_{10}H_{18}N_2Si.2HCl$ Calc.C 44.94; H 7.54; N 10.48; Si 10.51; Cl 26.53 Found:C 44.42; H 7.27; N 10.58; Si 10.70; Cl 26.07

Example 3

Synthesis of 2-[(trimethylsilanyl)ethyl]-para-phenylenediamine dihydrochloride

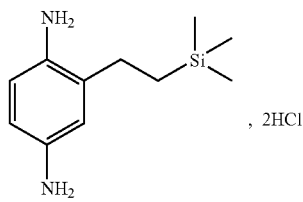

a/ First step: Synthesis of 2-iodo-4-nitroaniline 42.7 g (0.309 mol) of 4-nitroaniline were dissolved in the hot state (in the region of 80° C.) in 150 ml of acetic acid. A solution of 50 g (0.309 mol) of iodine monochloride in 100 ml of acetic acid was added dropwise thereto over 30 minutes. The mixture was kept stirred at 100° C. for 2 hours. By TLC, a trace of initial material remained. 1 g of iodine monochloride was therefore added and the mixture was kept stirred at 100° C. for 1 hour. The reaction mixture was filtered in the hot state. The solid was washed with ether and then dried. 74 g of a green-grey powder of 2-iodo-4-nitroaniline were thus obtained (yield of 91%). This product was used as is in the next step.

b/ Second step: Synthesis of 4-nitro-2-[(trimethylsilanyl)ethynyl]phenylamine 19.8 g (0.075 mol) of the preceding derivative, 1.6 g (2.25 mmol) of bis(triphenylphosphine)palladium(II)chloride, 0.86 g (4.5 mmol) of copper(I) iodide in 300 l of triethylamine were introduced into a reactor under argon bubbling. The mixture was cooled to around 3° C. and 13 ml (0.09 mol) of (trimethylsilyl)ethyne were introduced in portions over 20 minutes under an argon atmosphere. The mixture was kept at this temperature, with stirring, for 1 hour. The solvent was evaporated under vacuum. The residue was solubilized in the hot state in ethanol and treated with activated charcoal. The mixture was filtered on Celite, and the solvent was evaporated off. The residue was taken up in diethyl ether and the residue was removed by filtration. The organic phase was washed with an aqueous sodium chloride solution. It was dried and the solvent was evaporated under vacuum. The solid obtained was recrystallized from heptane to give 8.1 g (yield 47%) of 4-nitro-2-[(trimethylsilanyl)ethynyl]phenylamine in the form of yellow crystals. This product was used as is in the next step.

c/ Third step: Synthesis of 2-[(trimethylsilanyl)ethyl]-para-phenylenediamine dihydrochloride 6.75 g (0.029 mol) of the preceding derivative, 0.68 g of 5% palladium on carbon moistened with 50% of water, and 120 ml of absolute ethanol were introduced into a 250 ml hydrogenator. The hydrogenator was closed and, under hydrogen pressure (5 bar), the mixture was kept at 60° C. for 4 hours. After degassing with nitrogen, the reaction mixture was poured into 75 ml of ethanol containing 6 ml of concentrated hydrochloric acid (that is 66 meq). The solvent was evaporated to dryness and dried under vacuum. 6.75 g (yield of 84%) of the product from Example 1 were thus obtained in the form of an off-white powder.

Melting point: 140° C. (start of decomposition)–160° C. Elemental Analysis for $C_{11}H_{20}N_2Si.2HCl$ Calc.C 46.97; H 7.88; N 9.96; Si 9.98; Cl 25.21 Found:C 46.43; H 7.40; N 10.43; Si 9.45; Cl 25.80

Example 4

Synthesis of N-trimethylsilanylpropyl-para-phenylenediamine dihydrochloride

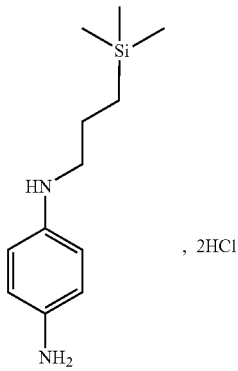

a/ First step: Synthesis of 3-trimethylsilylpropionic acid chloride 13.5 g (0.11 mol) of thionyl chloride were added dropwise at room temperature to a solution of 10 g (0.068 mol) of 3-trimethylsilylpropionic acid in 50 ml of 1,2-dichloroethane. The mixture was heated at 40° C. for 2 hours, and the excess thionyl chloride was distilled under vacuum. A solution of 3-trimethylsilylpropionic acid chloride was obtained in 1,2-dichloroethane, which solution was used as is in the next step.

b/ Second step: Synthesis of N-(4-nitrophenyl)-3-trimethylsilanylpropionamide 9.3 g (0.067 mol) of 4-nitroaniline and 7.1 g (0.07 mol) of triethylamine were dissolved in 50 ml of 1,2-dichloroethane. The solution obtained above was added dropwise thereto over 10 minutes. The mixture was kept stirred at 50° C. for 2 hours. The reaction mixture was poured into water, and the organic phase was separated, washed with acidulated water, and then with a bicarbonate solution, and finally with water.

After separation of the organic phase, drying over sodium sulfate and evaporation of the solvent, a brown oil was obtained. It was treated with activated charcoal at the reflux temperature of ethanol in order to decolourize it. The new crude material obtained was purified on silica (eluant: AcOEt/Heptane 1:2) to give 12.5 g of a grey powder of N-(4-nitrophenyl)-3-trimethylsilanylpropionamide (yield of 70%). This product was used as is in the next step.

c/Third step: Synthesis of (4-nitrophenyl)-(3-trimethylsilanylpropyl)amine 9.5 g (0.036 mol) of the preceding product were dissolved in 300 ml of anhydrous THF under argon bubbling. The medium was cooled to 0° C. and 2.1 g of lithium aluminium hydride were added in portions. The mixture was left for 1 hour at 0° C. and then for 2 hours under reflux. After cooling, the reaction mixture was hydrolysed with 25 ml of a THF/water mixture and then hot water. After filtration, the filtrate was evaporated off. The black oil obtained was purified by preparative chromatography on silica (eluant: AcOEt/Heptane 1:4). 2.1 g (yield of 23%) of pure fractions of (4-nitrophenyl)-(3-trimethylsilanylpropyl)amine were recovered in the form of an orange-coloured oil.

d/Fourth step: Synthesis of N-trimethylsilanylpropyl-para-phenylenediamine dihydrochloride 1.8 g (0.00713 mol) of the preceding derivative, 0.2 g of 5% palladium on carbon moistened with 50% of water and 120 ml of absolute ethanol were introduced into a 250 ml hydrogenator. The hydrogenator was closed and, under hydrogen pressure (4 bar), the mixture was kept at 40° C. for 4 hours. After degassing with nitrogen, the reaction mixture was poured into 80 ml of ethanol containing 1.5 ml of concentrated hydrochloric acid (that is 23 meq). The solvent was evaporated to dryness and dried under vacuum. The solid obtained was washed with ethyl acetate and then dried. 1.1 g (yield of 52%) of the product from Example 4 were thus obtained in the form of a pale beige powder.

Elemental Analysis for $C_{12}H_{22}N_2Si.2HCl$ Calc:C 48.8; H 8.19; N 9.49; Si 9.51; Cl 24.01 Found:C 48.96; H 8.00; N 9.44; Si 9.12; Cl 23.56

Example 5

Synthesis of 4-amino-3-(trimethylsilanylmethyl)phenol hydrochloride

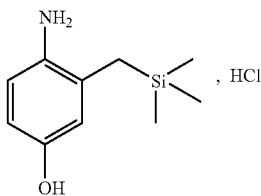

a/First step: Synthesis of 4-nitrotrimethylsilyloxybenzene:

15 g (0.138 mol) of 4-nitrophenol and 7.5 g (0.074 mol) of triethylamine were dissolved in 30 ml of THF, under argon bubbling. 15 g (0.138 mol) of trimethylsilyl chloride were introduced dropwise therein at room temperature. This mixture was heated under reflux for 2 hours 30 minutes. The reaction mixture was cooled. The triethylamine hydrochloride was separated by filtration. The solvent was removed by distillation under atmospheric pressure. After distillation under reduced pressure (0.3 mmHg) of the oil obtained, 12.1 g (yield of 85%) of the fractions distilling at 96–110° C. were recovered. This product was used as is in the next step.

b/Second step: Synthesis of 4-nitro-3-trimethylsilanylmethylphenol

The magnesium compound of chloromethyltrimethylsilane (Peterson's reagent) was first prepared in the following manner: 2.7 g of magnesium turnings (0.111 mol) were covered with a minimum of THF under inert argon gas. A few iodine crystals were introduced as well as one twentieth of the quantity of chloromethyltrimethylsilane (total quantity 13.3 g, 0.108 mol). A few drops of 1,2-dibromoethane were introduced and again one twentieth of the quantity of chloromethyltrimethylsilane was introduced. After heating, the reaction starts. The heating bath was reduced, and the remainder of the chloromethyltrimethylsilane dissolved in 60 ml of THF was introduced dropwise into the reaction mixture kept under reflux. This mixture was kept under reflux for 2 hours after the end of the introduction, and then it was cooled.

10.1 g (0.048 mol) of the product of step 1 were dissolved in 150 ml of THF in another round-bottomed flask. This mixture under argon atmosphere was cooled to −78° C. using a dry ice bath. The preceding magnesium compound was introduced therein over 1 hour using a small tube between the 2 round-bottomed flasks, while pushing with argon. The nitrone formed was then rearomatized using the dropwise introduction of 19 g (0.86 mol) of 2,3-dichloro-5,6-dicyanoquinone (DDQ) dissolved in 150 ml of THF over 20 minutes. The temperature of the reaction mixture was then gradually brought to room temperature. This mixture was poured into 380 ml of 5% acetic acid and was then extracted with dichloromethane. The organic phase was washed with a sodium bicarbonate solution and then with water. After drying with sodium sulphate and filtration, the solvent was evaporated under vacuum. The crude material obtained was extracted in the hot state with heptane to give a brown oil after evaporation of the solvent. The new crude material obtained was purified by preparative chromatography on silica (eluant: AcOEt/Heptane 1:3). 6.1 g (yield of 57%) of purified fractions of 4-nitro-3-trimethylsilanylmethylphenol were recovered.

c/Third step: Synthesis of 4-amino-3-(trimethylsilanylmethyl)phenol hydrochloride:

5.8 g (0.026 mol) of the preceding derivative, 0.6 g of 5% palladium on carbon moistened with 50% of water, and 120 ml of absolute ethanol were introduced into a 250 ml hydrogenator. The hydrogenator was closed and, under hydrogen pressure (6 bar), the mixture was kept at 60° C. for 4 hours. After degassing with nitrogen, the reaction mixture was poured into 80 ml of ethanol containing 3 ml of concentrated hydrochloric acid (that is 36 meq). The solvent was evaporated to dryness and dried under vacuum. The solid obtained was washed with ethyl acetate and then dried. 2.75 g (yield of 46%) of the product from Example 5 were thus obtained in the form of a pale beige powder.

Elemental Analysis for $C_{10}H_{17}NOSi.HCl$ Calc:C 51.82; H 7.83; N 6.04, Si 12.12; Cl 15.29 Found:C 51.85; H 7.77; N 6.16; Si 11.87; Cl 15.64

Examples of Dyeing

The following dyeing compositions were prepared (amounts in mols):

| Examples | 1 | 2 |
|---|---|---|
| 2-trimethylsilanylmethoxy-para-phenylenediamine dihydrochloride | $3 \times 10^{-3}$ mol | — |
| 1-β-hydroxyethyloxy-2,4-diaminobenzene.2HCl | $3 \times 10^{-3}$ mol | $3 \times 10^{-3}$ mol |
| Para-phenylenediamine | — | $3 \times 10^{-3}$ mol |
| Dye carrier (1) | (*) | (*) |
| Demineralized water q.s. | 100 g | 100 g |

* Dye carrier (1) pH = 9.5

| | |
|---|---|
| Ethyl alcohol at 96° | 18 g |
| Sodium metabisulfite as aqueous solution at 35% | 0.68 g |
| Pentasodium salt of diethylene-triaminopentaacetic acid | 1.1 g |
| Aqueous ammonia at 20% | 10 g |

At the time of use, each composition was mixed with an equal weight of hydrogen peroxide at 20 volumes (6% by weight).

Each mixture obtained was applied to locks of grey hair which is 90% white, permanently waved (BP) or natural (BN). After an exposure time of 30 min, the locks were rinsed, washed with a standard shampoo, rinsed again and then dried.

Each lock was evaluated before and after dyeing in the L*a*b* system, using a MINOLTA CM 2002® spectrophotometer (illuminant D65).

In the space L*a*b*, the clarity is indicated by the value L* on a scale from 0 to 100 whereas the chromatic co-ordinates are expressed by a* and b* which indicate two colour axes, a* the green-red axis, and b* the blue-yellow axis.

According to this system, the higher the value of L*, the lighter and the less intense the colour. Conversely, the lower the value of L*, the darker or more highly intense the colour.

The following dyeing results were obtained.

| | Natural hair | | | Permanently waved hair | | |
|---|---|---|---|---|---|---|
| | L* | a* | b* | L* | a* | b* |
| Example 1 | 22.3 | 0.08 | −5.4 | 19.7 | 0.8 | −2.3 |

In a second series of tests, the resistance to shampoos of the dye obtained from Example 1 (invention) and from Example 2 (control) on permanently waved hair was measured.

For each lock, the values L*, a*, and b* were measured before the shampoo test and after 8 shampoos.

The results are presented in the following table

| | Before shampoo | | | After 8 shampoos | | |
|---|---|---|---|---|---|---|
| | L* | a* | b* | L* | a* | b* |
| Example 1 | 18.6 | 0.2 | −1.3 | 19.3 | −0.1 | −1.1 |
| Example 2 | 18.7 | 0.6 | −2.2 | 27.1 | 2.6 | 1.3 |

What is claimed is:

1. A dyeing composition, comprising:
   a medium appropriate for dyeing keratinous fibers and
   at least one oxidation base in said medium, wherein said at least one oxidation base is chosen from compounds corresponding to the following formula (I) and the corresponding cosmetically acceptable salts thereof:

wherein:
   A is chosen from OH and $NH_2$;
   $R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;
   $R_3$ and $R_4$, which may be identical or different, are chosen from hydrogen, $C_1$–$C_4$ alkyl radicals, $C_1$–$C_4$ alkoxy radicals, halogen atoms, and —Z—B radicals;
   Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;
   Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR''—Y radicals, wherein R'' is chosen from hydrogen and $C_1$–$C_4$ alkyl radicals; and
   B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and Z—B.

2. The composition according to claim 1, wherein $R_1$ is a hydrogen atom.

3. The composition according to claim 1, wherein at least one of $R_3$ and $R_4$ is a hydrogen atom.

4. The composition according to claim 1, wherein $R_1$ and $R_2$ are each a hydrogen atom.

5. The composition according to claim 1, wherein $R_1$ and $R_2$ form with the nitrogen atom to which they are attached a 5- or 6-membered heterocycle wherein the heterocycle is substituted with the group —Z—B.

6. The composition according to claim 5, wherein $R_3$ and $R_4$ are each a hydrogen atom.

7. The composition according to claim 1, wherein the compound of formula (I) is chosen from the following compounds and the acid addition salts of these compounds:

2-trimethylsilanylmethoxy-para-phenylenediamine
N-trimethylsilanylmethyl-para-phenylenediamine
2-[(trimethylsilanyl)ethyl]-para-phenylenediamine
N-trimethylsilanylpropyl-para-phenylenediamine
2-(trimethylsilanyl)-para-phenylenediamine
2,5-di-(trimethylsilanyl)-para-phenylenediamine
2-trimethylsilanylethoxy-para-phenylenediamine
4-amino-3-(trimethylsilanylmethyl)phenol, and
4-amino-3-(trimethylsilanyl)phenol.

8. The composition according to claim 1, wherein the at least one oxidation base is present in an amount ranging from about 0.0005 to about 12% by weight relative to the total weight of the dyeing composition.

9. The composition according to claim 1, further comprising at least one additional oxidation base chosen from para-phenylenediamines, bis-phenylalkylenediamines, para-aminophenols, ortho-aminophenols, heterocyclic bases, and their acid and base addition salts.

10. The composition according to claim 1, further comprising at least one direct dye.

11. The composition according to claim 1, further comprising at least one oxidizing agent.

12. A method for oxidation dyeing of keratinous fibers comprising applying to the keratinous fibers, in the presence of at least one oxidizing agent, a composition comprising at least one oxidation base chosen from compounds corresponding to the following formula (I) and the corresponding cosmetically acceptable salts thereof:

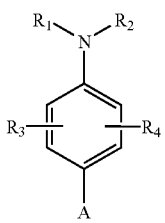

(I)

wherein:
A is chosen from OH and $NH_2$;
$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;
$R_3$ and $R_4$, which may be identical or different, are chosen from hydrogen, $C_1$–$C_4$ alkyl radicals, $C_1$–$C_4$ alkoxy radicals, halogen atoms, and Z—B radicals;
Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;
Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals;

B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—.

13. The method according to claim 12, wherein the keratinous fibers are human keratinous fibers.

14. The method according to claim 13, wherein the human keratinous fibers are hair.

15. The method according to claim 12, wherein the at least one oxidizing agent is chosen from hydrogen peroxide, urea peroxide, alkali metal bromates, persalts, peracids, and oxidase enzymes.

16. The method according to claim 12, wherein the at least one oxidizing agent is mixed with the composition at the time of use.

17. The method according to claim 12, wherein the at least one oxidizing agent is applied to the keratin fibers in the form of an oxidizing composition, simultaneously with or sequentially to the composition.

18. A multi-compartment device or multi-compartment dyeing kit comprising a first compartment comprising a composition comprising at least one oxidation base chosen from compounds corresponding to the following formula (I) and the corresponding cosmetically acceptable salts thereof:

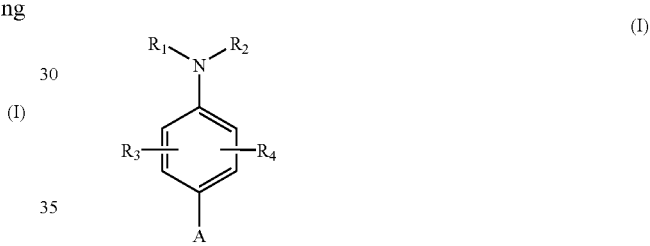

wherein:
A is chosen from OH and $NH_2$;
$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;
$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;
Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;
Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals;
B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B, and a second compartment comprising an oxidizing composition.

19. A coloured product obtained by oxidation of a composition comprising:

a medium appropriate for dyeing keratinous fibers and at least one oxidation base in said medium, wherein said at least one oxidation base is chosen from compounds corresponding to the following formula (I) and the corresponding cosmetically acceptable salts thereof:

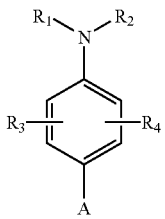

(I)

wherein:

A is chosen from OH and $NH_2$;

$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;

$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;

Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;

Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals; and B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B.

20. A method of manufacturing a coloured product comprising oxidizing a composition comprising at least one oxidation base chosen from compounds corresponding to the following formula (I) and the corresponding cosmetically acceptable salts thereof:

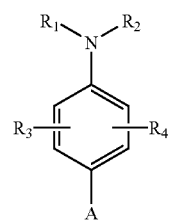

(I)

wherein:

A is chosen from OH and $NH_2$;

$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;

$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;

Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;

Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals;

B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B.

21. A composition for dyeing keratinous fibers comprising a medium appropriate for dyeing keratinous fibers and at least one oxidation base in said medium, wherein said at least one oxidation base is chosen from compounds corresponding to the following formula (I) and the corresponding cosmetically acceptable salts thereof:

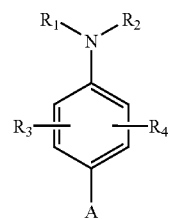

(I)

wherein:

A is chosen from OH and $NH_2$;

$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;

$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;

Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;

Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $C_1$–$C_4$ alkyl radicals; and B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B; and wherein the composition is effective in dyeing keratinous fibers.

22. A method for dyeing keratinous fibers comprising applying to the keratinous fibers a composition comprising a medium appropriate for dyeing keratinous fibers and at least one oxidation base in said medium, wherein said at least one oxidation base is chosen from compounds corresponding to the following formula (I) and the corresponding cosmetically acceptable salts thereof:

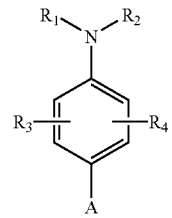

(I)

wherein:

A is chosen from OH and $NH_2$;

$R_1$ and $R_2$, which may be identical or different, are chosen from hydrogen, linear and branched $C_1$–$C_8$ alkyl radicals, $C_1$–$C_6$ hydroxyalkyl radicals, and —Y—B radicals; $R_1$ and $R_2$ may form, together with the nitrogen atom to which they are attached, a 4- to 7-membered heterocycle, optionally substituted with at least one group chosen from $C_1$–$C_3$ alkyls, OH, $NH_2$ and Z—B radicals; provided that when A is OH, then $R_1$ and $R_2$ are each hydrogen;

$R_3$ and $R_4$, which may be identical or different, are chosen from hydrogen, $C_1$–$C_4$ alkyl radicals, $C_1$–$C_4$ alkoxy radicals, halogen atoms, and —Z—B radicals;

Y is chosen from saturated and unsaturated, linear and branched $C_1$–$C_8$ hydrocarbon chains that may include at least one hetero atom chosen from O, S, and NR, wherein R is chosen from hydrogen and $C_1$–$C_4$ alkyl radicals;

Z is chosen from a covalent bond, and saturated and unsaturated, linear and branched $C_1$–$C_8$ hydrocarbon chains that may include at least one hetero atom chosen from O, S, and NR', wherein R' is chosen from hydrogen, $C_1$–$C_4$ alkyl radicals, O—Y radicals, and NR"—Y radicals, wherein R" is chosen from hydrogen and $R_1$–$C_4$ alkyl radicals;

B is chosen from —$SiR_5R_6R_7$ groups, wherein $R_5$, $R_6$, and $R_7$, which may be identical or different, are chosen from $C_1$–$C_4$ alkyl and phenyl radicals; provided that at least one of the groups $R_1$, $R_2$, $R_3$, and $R_4$ is chosen from —Y—B and —Z—B.

* * * * *

UNITED STATES PATENT AND TRADEMARK OFFICE
CERTIFICATE OF CORRECTION

| | | |
|---|---|---|
| PATENT NO. | : 7,018,427 B2 | Page 1 of 1 |
| APPLICATION NO. | : 10/259298 | |
| DATED | : March 28, 2006 | |
| INVENTOR(S) | : Hervé Richard | |

It is certified that error appears in the above-identified patent and that said Letters Patent is hereby corrected as shown below:

In claim 12, column 18, line 5, "–Z–." should read -- –Z-B.--

In claim 22, column 22, line 39, "$R_1$-$C_4$" should read --$C_1$-$C_4$--.

Signed and Sealed this

Twenty-second Day of August, 2006

JON W. DUDAS
*Director of the United States Patent and Trademark Office*